(12) United States Patent
De Winter

(10) Patent No.: US 7,749,239 B2
(45) Date of Patent: Jul. 6, 2010

(54) SCREW-DEVICE FOR ANASTOMOSIS

(76) Inventor: Erwin De Winter, Pol De Montstraat 6, Antwerpen (BE) 2020

( * ) Notice: Subject to any disclaimer, the term of this patent is extended or adjusted under 35 U.S.C. 154(b) by 518 days.

(21) Appl. No.: 10/554,986

(22) PCT Filed: Jul. 22, 2003

(86) PCT No.: PCT/BE03/00126

§ 371 (c)(1),
(2), (4) Date: Feb. 2, 2006

(87) PCT Pub. No.: WO2004/096059

PCT Pub. Date: Nov. 11, 2004

(65) Prior Publication Data

US 2006/0259050 A1    Nov. 16, 2006

(30) Foreign Application Priority Data

Apr. 28, 2003    (BE) .................................. 03/00074

(51) Int. Cl.
*A61B 17/08*    (2006.01)
(52) U.S. Cl. ...................................... 606/153; 606/143
(58) Field of Classification Search ................ 606/151, 606/153, 155, 232, 143, 148, 191, 213
See application file for complete search history.

(56) References Cited

U.S. PATENT DOCUMENTS

| 4,495,007 | A |   | 1/1985  | Zado              |         |
|-----------|---|---|---------|-------------------|---------|
| 4,762,453 | A | * | 8/1988  | DeCaro            | 411/383 |
| 5,163,343 | A |   | 11/1992 | Gish              |         |
| 5,370,662 | A | * | 12/1994 | Stone et al.      | 606/232 |
| 5,437,266 | A | * | 8/1995  | McPherson et al.  | 600/217 |
| 5,662,683 | A | * | 9/1997  | Kay               | 606/232 |
| 5,671,773 | A |   | 9/1997  | Park              |         |
| 5,755,697 | A |   | 5/1998  | Jones et al.      |         |
| 5,810,882 | A |   | 9/1998  | Bolduc et al.     |         |
| 5,891,100 | A |   | 4/1999  | Fleckenstein      |         |

(Continued)

FOREIGN PATENT DOCUMENTS

DE    19826078 C1    8/1999

OTHER PUBLICATIONS

Aug. 7, 2008 Office Action from co-pending U.S. Appl. No. 10/554,947.

*Primary Examiner*—(Jackie) Tan-Uyen T Ho
*Assistant Examiner*—Jing Ou
(74) *Attorney, Agent, or Firm*—Browdy and Neimark, PLLC

(57) ABSTRACT

The present invention, the screw-device, is a mechanical device for anastomosing hollow tube-like structures in the human body, such as blood vessels, bowels and ureters. It is thus not restricted to (micro-) vessels. It can be used in every surgical operation dealing with anastomosis and bypass operations. It allows anastomosing end to side or side to side. The screw-device is very easy to apply onto the vessel wall. Screwing is a fast technique saving operating time and requiring only basic microsurgical skills. The manufacturing is easy. Another advantage is that the screw-device can be mounted onto the receptor vessel without first opening and/or occluding this vessel. Later on, the receptor vessel wall can be opened with laser or scalpel. It should be understood that the foregoing is illustrative and not limiting, and that modifications may be made by those skilled in the art, without departing from the scope of the invention.

10 Claims, 6 Drawing Sheets

U.S. PATENT DOCUMENTS

| | | |
|---|---|---|
| 6,113,611 A | 9/2000 | Allen et al. |
| 6,132,438 A | 10/2000 | Fleischman et al. |
| 6,171,320 B1 | 1/2001 | Monassevitch |
| 6,210,397 B1 | 4/2001 | Aboul-Hosn et al. |
| 6,663,633 B1 * | 12/2003 | Pierson, III .................. 606/148 |
| 2002/0013605 A1 | 1/2002 | Bolduc et al. |
| 2003/0014127 A1 | 1/2003 | Talja et al. |
| 2003/0100943 A1 * | 5/2003 | Bolduc ....................... 623/1.35 |

* cited by examiner

SCREW-DEVICE FOR ANASTOMOSIS

TECHNICAL FIELD

The present invention relates to an anastomosis device, more particularly, the SCREW-DEVICE is capable of anastomosing the end of a blood vessel to the side of another blood vessel (end to side—see FIG. 1) or the side of a blood vessel to the side of another blood vessel (side to side—see FIG. 2).

BACKGROUND ART

Vital Cells (in brain, heart, muscles, organs) demand nutrition, oxygen, energy (glucose) at a constant supply. These components are found in the blood which runs in a healthy vascular system. As a pump system, the heart ensures the circulation of the blood (nutrients) through the body. When there is a discrepancy between demand of oxygen or nutrients to the cell and the delivery capacity of the bloodstream to the cell, there is cell damage or even cell death. In some vital organs this warm ischemia before cell death is very short. For brain cells, death occurs after 3 minutes. The reason for this insufficiency is mostly a vascular disease (arteriosclerosis), stenosis, occlusion of small or large vessels, or a heart problem (coronary disease). Most important risk factors of arteriosclerosis are: hypertension, elevated serum lipids, cigarette smoking, diabetes mellitus, decreased physical activity and obesitas (i.e., consuming more calories than those expended as energy).

Treatment Options

To treat a clogged or occluded blood vessel, PHARMACOTHERAPY and SURGERY have been practiced. Pharmacotherapy is useful for treatment at the initial stage but not when there is further progression of the disease, leading to occlusion of the vessel and eventually to an infarct (of the heart, brain, kidney. etc).

The medical diagnostic tools and the technical developments available to the doctor have increased enormously, MRI-, MRA-, CT- and CTA-scan. This has enabled an early diagnosis and a more successful treatment of patients with vascular diseases.

In vascular surgery we have, firstly, the endovascular procedures, for example: stents, which can expand the occluded vessel in heart surgery (coronary artery) and in vascular surgery (stenosis of the carotic artery); stents remodelling aneurysma of the aorta abdominals; and recently the brain stents remodelling fusiform aneurysma of the basilar artery.

In vascular surgery we have, secondly, the revascularisation operations, viz. anastomosis and bypass operations. These revascularisation operations are carried out when there is (risk of) ischaemia, (risk of) infarct (of the heart, brain, limb, etc). Bypass procedures in general vascular surgery, in heart surgery (coronary bypass), and in neurosurgery want to bypass huge vascular malformations (giant aneurysmas). In tumor surgery, bypass operations want to avoid the risk of brain-infarct after and/or before removing the tumor.

The graft can be an arterial graft (in the case of heart surgery it would be the lima, or rima; in the case of neurosurgery, it would be the temporal artery or the occipital artery), or a venous graft (v.s.m), or even prosthetic material. These highly complex operations require a competent surgical team, delicate instruments, advanced microsurgical equipment, magnifying loops, or—for neurosurgeons—an operating microscope.

In microvascular surgery, ultra fine suture material is used to suture the blood vessels onto each other (anastomosis). This technique of suturing is time consuming and it demands extremely advanced microsurgical skills. Moreover, it never results in a completely smooth joint, the stitches producing microscopic creases in the vessel wall. Various methods have been developed to perform anastomosis with mechanical devices in a short time without suturing. Most of these devices are complex and time-consuming to apply (for example, in brain-surgery, a microvascular anastomosis takes on average, twenty to thirty minutes).

During this time, there is a high risk of bleeding and infection in all forms of microvascular surgery mentioned above. Reducing this time is of the utmost importance for the well-being of the patient.

SUMMARY OF INVENTION

The object was to invent a really easy and extremely quick way to perform vascular anastomosis.

The present invention, the SCREW-DEVICE, provides a device capable of anastomosing the side of a vessel to another vessel (side to side) or the end of a vessel to the side of another vessel (end to side) without use of a suture. As a result there is a perfectly smooth joint, without any creases in the vessel wall.

The SCREW-DEVICE is very easy to apply on the vessel wall, it takes only a few seconds to screw the SCREW-DEVICE into the vessel wall of the receptor vessel and to screw it into the donor vessel. This procedure can also be reversed, screwing the device into the donor vessel and screwing this onto the receptor vessel.

It can be used in every surgical operation dealing with vascular problems, like anastomosis or bypass operations done in vascular surgery, heart surgery and neurosurgery.

The opening of the receptor vessel wall can be done without occlusion of the receptor vessel or with a temporary occlusion of the receptor vessel. It can easily be combined with existing laser technologies for opening the receptor vessel in a non-occlusive manner.

DETAILED DESCRIPTION

Form: There are five main forms.

1. SINGLE-ENDED SCREW-DEVICE. This device 100 is a spring with four to six windings guaranteeing elasticity. The first three windings are closely adjacent, i.e. there is just the smallest space between them (the space enabling the SCREW-DEVICE to dig itself into the vessel wall). On the one end of the SINGLE-ENDED SCREW-DEVICE there is an extremely sharp end, meant to perforate the vessel wall. The other end is blunt.

Figure 1:
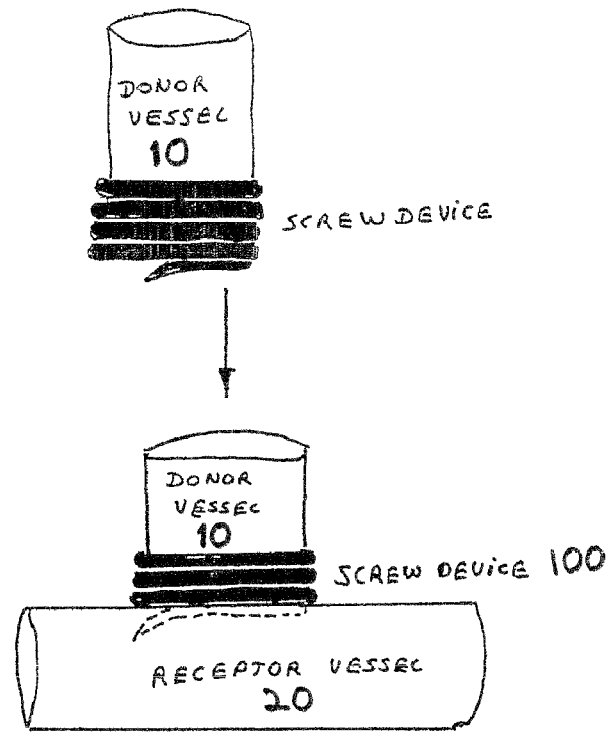
FIG. 1: Anastomosis with the SCREW-DEVICE end to side.
Figure 2:
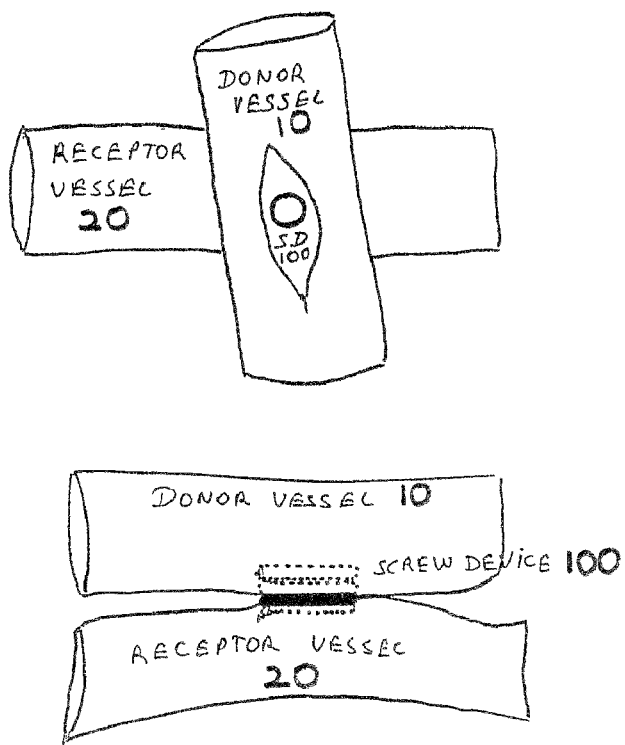
FIG. 2: Anastomosis with the SCREW-DEVICE side to side.
Figure 3A:
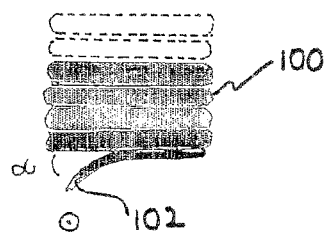
FIG. 3a: Lateral view of SINGLE-ENDED SCREW-DEVICE.
Figure 3E:
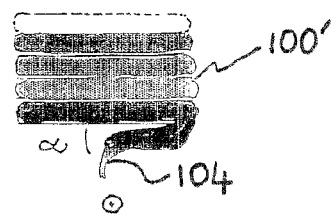
FIG. 3b: Top view of SINGLE-ENDED SCREW-DEVICE.
FIG. 3c: Inside view: inside the receptor vessel of SINGLE-ENDED SCREW-DEVICE.
FIG. 3d: SINGLE-ENDED SCREW-DEVICE screwed into the donor vessel.
Figure 3B:
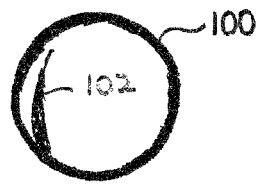
Figure 3C:
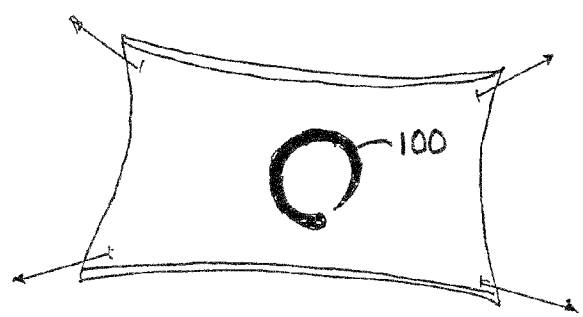
Figure 3D:
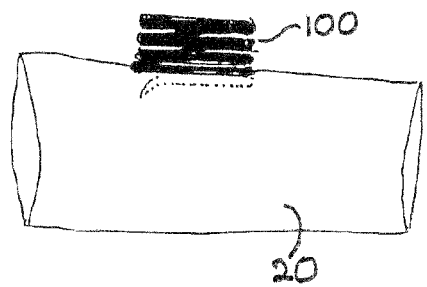

The sharp end 102 is round, i.e. non-cutting but capable of perforating the vessel wall. The sharp, round point is bent inwardly and downwardly in an angle of 10 to 20 degrees (a) (see FIG. 3a, 3b, 3c, 3d). Alternatively, as seen in FIG. 3e, the device 100' has a sharp, round, non-cutting point 104, which may bend downwardly in an angle of 90 degrees (a). In this case, the end resembles a corkscrew, but the end is not situated in the middle of the final winding but rather on the periphery.

Figure 4A:
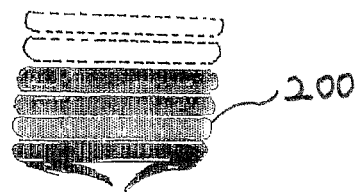
FIG. 4a: Lateral view of DOUBLE-ENDED SCREW-DEVICE/RING-FORM.
Figure 4B:
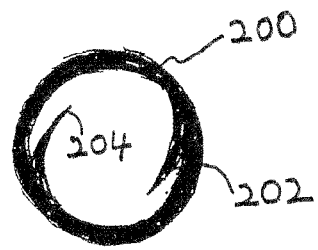
FIG. 4b: Top view of DOUBLE-ENDED SCREW-DEVICE/RING-FORM.
Figure 4C:
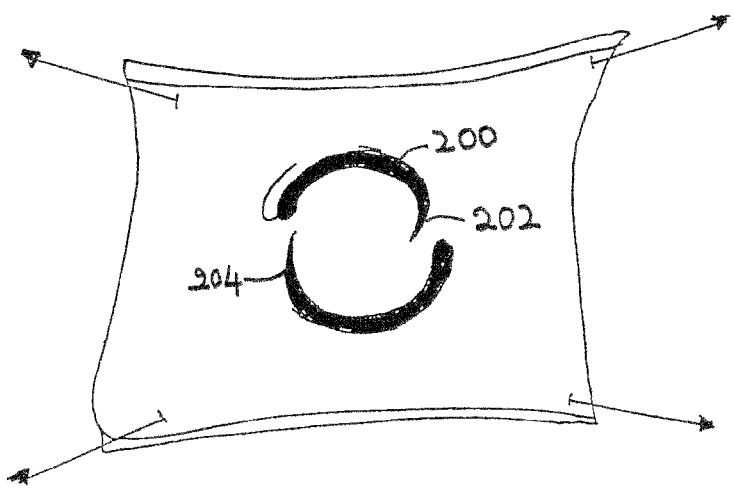
FIG. 4c: Inside view: inside the receptor vessel of DOUBLE-ENDED SCREW-DEVICE/RING-FORM.
Figure 5A:
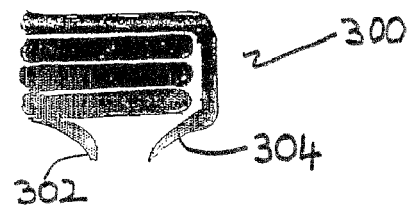
FIG. 5a: Lateral view of DOUBLE-ENDED SCREW-DEVICE/SPIRAL FORM.
Figure 5B:
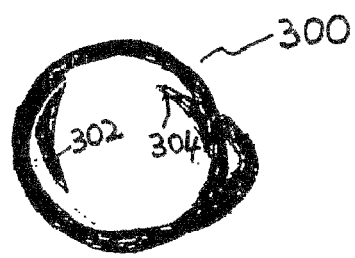
FIG. 5b: Top view of DOUBLE-ENDED SCREW-DEVICE/SPIRAL FORM.

2. DOUBLE-ENDED SCREW-DEVICE/RING-FORM. This device 200 is a spring with four to six windings guaranteeing elasticity. The first three windings are closely adjacent, i.e. there is just the smallest space between them (the space enabling the SCREW-DEVICE to dig itself into the vessel wall). On the one end the DOUBLE-ENDED SCREW-DEVICE/RING-FORM takes the form of a ring, with two sharp, round, non-cutting points 202, 204, pointing in the same direction but 180 degrees apart from each other (see FIG. 4a, 4b, 4c). These two points are bent inwardly and downwardly in an angle of 10 to 20 degrees. Alternatively, these sharp, round, non-cutting points may bend downwardly in an angle of 90 degrees (like to the point shown in FIG. 3e). In this case, they resemble a corkscrew, but the ends are not situated in the middle of the final winding but rather on the periphery. The other end of the DOUBLE-ENDED SCREW-DEVICE is blunt.

3. DOUBLE-ENDED SCREW-DEVICE/SPIRAL FORM. This device 300 is a spring with four to six windings guaranteeing elasticity. The first three windings are closely adjacent, i.e. there is just the smallest space between them (the space enabling the SCREW-DEVICE to dig itself into the vessel wall). The DOUBLE-ENDED SCREW DEVICE/SPIRAL-FORM consists of two sharp, round, non-cutting points, the first point 302 coming from the end, the second point 304 coming from the beginning but bent in such a way as to align itself with the other sharp point (see FIG. Sa. 5b). Again, these two points point in the same direction but stand 180 degrees apart from each other. They bend inwardly and downwardly in an angle of 10 to 20 degrees. Alternatively, these sharp, round, non-cutting points may bend downwardly in an angle of 90 degrees (like to the point shown in FIG. 3e). In this case, the end resembles a cork-screw, but the ends are not situated in the middle of the final winding but rather on the periphery.

Figure 6A:
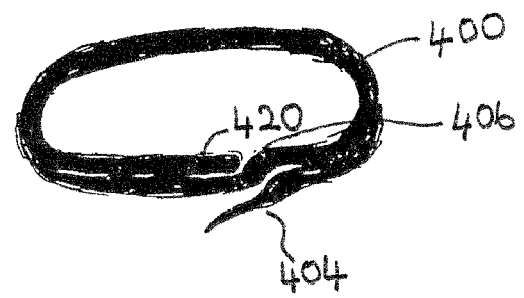
FIG. 6a: Lateral view of KEY-RING SCREW-DEVICE.
Figure 6B:
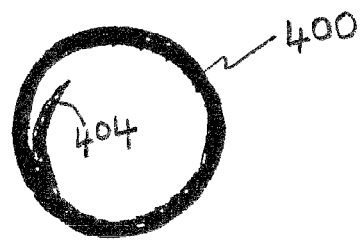
FIG. 6b: Top view of KEY-RING SCREW-DEVICE.

4. KEY-RING SCREW-DEVICE. This device 400 consists of two to three windings, resembling a key-ring. On the one end, there is a sharp, round, non-cutting point 404, bending inwardly and downwardly in an angle of 10 to 20 degrees. Alternatively, this point may bend downwardly in an angle of 90 degrees. In this case, the end resembles a cork-screw, but the end is not situated in the middle of the final winding but rather on the periphery. The other end 402 is blunt. Where the two ends meet, there is a twist 406 in the ring (see FIG. 6a, 6b).

5. SCREW-DEVICE WITH REMOVABLE HEAD. This device 500 consists of two basic parts, the removable head 502 (with applicator 504) and a hollow screw of three windings, which remains in place (i.e. in the blood-vessel).

Figure 7A:
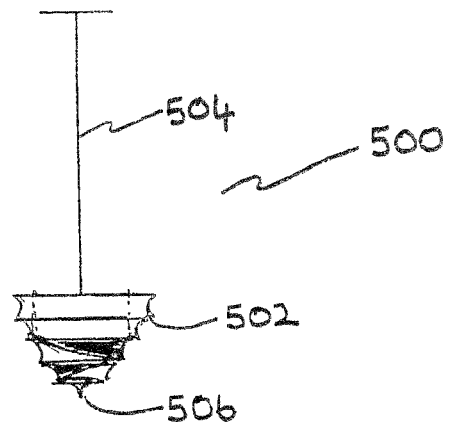
FIG. 7a: Lateral view of SCREW-DEVICE WITH REMOVABLE HEAD.
Figure 7B:
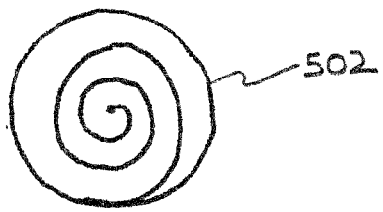
FIG. 7b: Top view of SCREW-DEVICE WITH REMOVABLE HEAD.
Figure 7C:
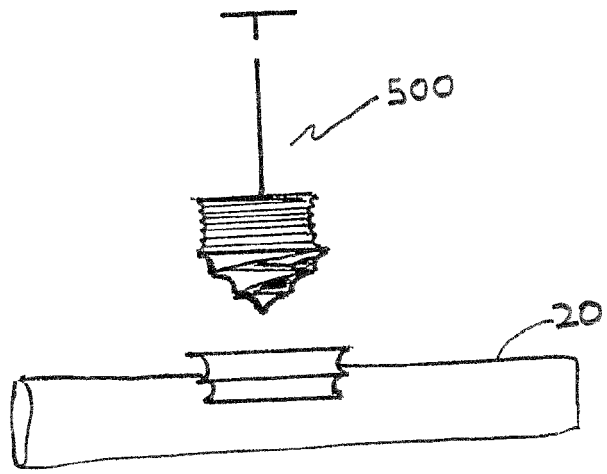
FIG. 7c: In situ view: position of SCREW-DEVICE WITH REMOVABLE HEAD in the vessel wall.

5.1. The head 502 consists of two windings, and ends in the form of a cork-screw (see FIG. 7a, 7b). This is, again, a round, sharp, non-cutting point 506. The head forms one whole with the applicator 504, i.e. a long, thin shaft with a handle used to drill the head into the vessel wall. Once the head is in place (i.e. in the middle of the vessel (see FIG. 7c), it is removed—together with the applicator—from the rest of the SCREW-DEVICE that stays within the vessel wall.

Figure 7D:
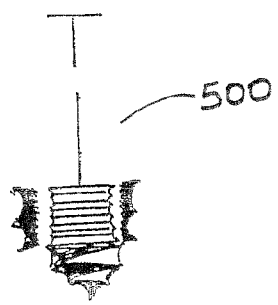
FIG. 7d: View of the way in which the removable head is attached to the remainder of the SCREW-DEVICE WITH REMOVABLE HEAD.

5.2. The other part of the SCREW-DEVICE consists of three hollow windings attached to the head by means of internal, anti-clockwise windings (see FIG. 7d). Every winding is wider than the previous one, thus expanding the vessel wall and the opening in it made by the head. This opening is made in a non-occlusive way, i.e. the receptor vessel need not be temporarily occluded.

Additional tool. In the fifth form, i.e. the SCREW-DEVICE WITH REMOVABLE HEAD, no additional tools are needed to open the vessel wall.

Figure 8A:
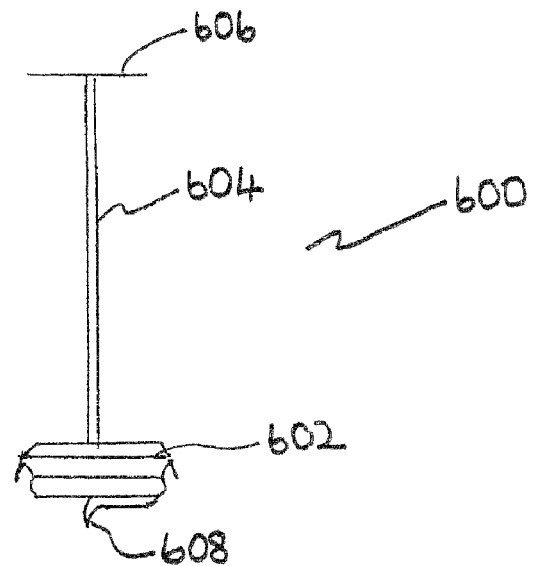
FIG. 8a: Lateral view of the SCREW-CUTTER.
Figure 8B:
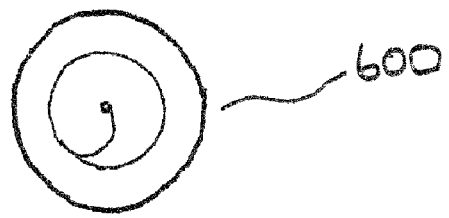
FIG. 8b: Top view of the SCREW-CUTTER.
Figure 8C:
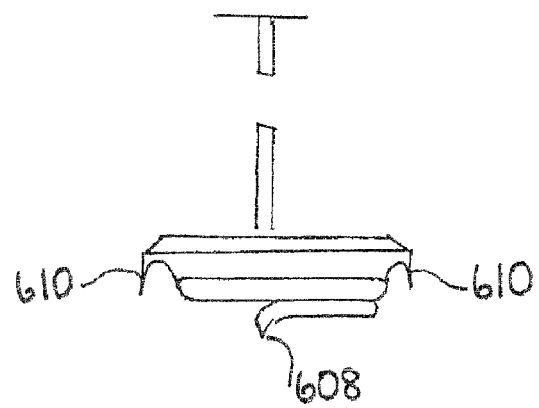
FIG. 8c: View of sharp end of SCREW-CUTTER, consisting of two regular windings and one sharp winding.

In the other forms, the hole in the vessel wall can be made by traditional means—basically: the occlusive manner using a surgical knife, or the non-occlusive manner using a laser—or by means of a SCREW-CUTTER. This specially designed device 600 operates in a non-occlusive manner. It takes the form of a hollow cylinder in which a long shaft 604 with a handle 606 on top moves up and down (see FIG. 8a, 8b). This shaft ends in a screw 602 consisting of three windings. The first two of these take the form of a cork-screw, so that the sharp point 608 is in the middle. They keep the vessel wall in its place, whereas the third winding—forming a full circle of 360 degrees—actually cuts and removes the part of the vessel wall where the hole is to be made. The third winding has its sharp edges 610 pointing downward, whereas the first two windings are horizontal, like in an ordinary screw (see FIG. 8c).

Diameter: Depending on the sort of blood-vessel, the diameter of the five SCREW-DEVICES may vary from 1 millimeter to plus 2 centimeter.

Substance: The SCREW-DEVICE is made of inox material, or titanium, or super-elastic materials such as nitinol, or synthetic materials, or even resorbable materials.

Thickness of material: Depending on the diameter of the blood-vessel, the material may vary from 0.1 mm to any desirable thickness.

Elasticity: Depending on the material.

DESCRIPTION OF OPERATION TECHNIQUE WITH THE SCREW-DEVICE

A. For the first four forms of the SCREW-DEVICE—that is: SINGLE-ENDED SCREW-DEVICE, DOUBLE-ENDED SCREW-DEVICE/RING-FORM, DOUBLE-ENDED SCREW-DEVICE/SPIRAL-FORM, KEY-RING SCREW-DEVICE—the technique is as follows:

1. End-to-side

In the first step, the receptor vessel is exposed by means of the techniques current in vascular surgery. When a venous graft is used end-to-side, the SCREW-DEVICE is screwed into the graft (donor vessel) or sutured to the donor vessel.

In the second step, the donor vessel containing the SCREW-DEVICE is screwed into the receptor vessel.

Alternatively, the SCREW-DEVICE can first be screwed into the receptor vessel and then the donor vessel can be attached to it.

The SCREW-DEVICE is turned into the vessel clock-wise and completes only one turn, that is: it is in its proper place after 360 degrees.

In the third step, the wall of the receptor vessel is opened by means of existing techniques, such as laser or the surgical knife.

2. Side-to-side

First, the donor vessel is clamped and opened. The SCREW-DEVICE is screwed into and through the vessel wall, thus perforating the donor vessel with two windings. These windings are then screwed into the receptor vessel (clockwise and 360 degrees). A hole is then made into the receptor vessel wall by means of existing techniques, such as laser or the surgical knife.

B. For the fifth form, that is the SCREW-DEVICE WITH REMOVABLE HEAD, the techniques mentioned sub A are applied in the same way, but they are followed by the removal of the head.

In all these forms, the SCREW-DEVICE can be used in an occlusive or non-occlusive manner, depending on the preferences of the surgeon.

MANUFACTURING AND INDUSTRIAL APPLICABILITY

The SCREW-DEVICE can be manufactured commercially and be employed to anastomose two vessels of different or identical sizes. It can be used in all domains of vascular surgery, heart surgery, and neurosurgery.

What is claimed is:

1. Method for anastomosing a receptor vessel and a donor vessel, these vessels being hollow tube-like structures of the human body and having walls with a given thickness, the method comprising the steps of providing a screw-device comprising a screw-like spiral spring with several windings, wherein the windings of the screw-like spiral spring are closely adjacent with a predetermined narrow space between them, said predetermined narrow space corresponding to the thickness of the vessel walls, and wherein a front winding of the screw-device has a sharp and round end and the screw-device is fully open at a rear winding and inwardly from the plurality of windings;

perforating the vessel wall of the receptor vessel using a sharp and round end of the front winding of the screw-device, screwing said screw-device into the vessel wall of the receptor vessel until the vessel wall is held between the closely adjacent windings of the screw-device, then screwing the screw-device into the donor vessel, and then opening the part of the vessel wall of the receptor vessel which is held between the closely adjacent windings of the screw-device.

2. Method according to claim 1, further comprising the step of opening the vessel wall of the receptor vessel using a screw-cutter for cutting a hole in a vessel wall, the screw-cutter comprising a hollow cylinder in which a long shaft with a handle on top moves up and down, the shaft ending in a screw consisting of three windings, the first two of which take the form of a cork-screw with horizontal winding and a sharp point on the middle, the third winding forming a full circle of 360 degrees and having sharp edges pointing downwards for actually cutting and removing part of the vessel wall, without occlusion of the receptor vessel.

3. Method according to claim 1, wherein the vessels are blood vessels.

4. Method according to claim 1, wherein the vessels are ureters.

5. Method according to claim 1, wherein the vessels are tracheae.

6. Method for anastomosing a receptor vessel and a donor vessel, these vessels being hollow tube-like structures of the human body and having walls with a given thickness, the method comprising the steps of providing a screw-device comprising a screw-like spiral spring with several windings, wherein the windings of the screw-like spiral spring are closely adjacent with a predetermined narrow space between them, said predetermined narrow space corresponding to the thickness of the vessel walls, and wherein a front winding of the screw-device has a sharp and round end and the screw-device is fully open at a rear winding and inwardly from the plurality of windings;

screwing the screw-device into the vessel wall of the donor vessel, perforating the vessel wall of the receptor vessel using the sharp and round end of the front winding of the screw device, then screwing the screw-device into the receptor vessel until the vessel wall is held between the closely adjacent windings of the screw-device, and then opening the part of the vessel wall of the receptor vessel which is held between the closely adjacent windings of the screw-device.

7. Method according to claim 6, further comprising the step of opening the vessel wall of the receptor vessel using a screw-cutter for cutting a hole in a vessel wall, the screw-cutter comprising a hollow cylinder in which a long shaft with a handle on top moves up and down, the shaft ending in a screw consisting of three windings, the first two of which take the form of a cork-screw with horizontal winding and a sharp point on the middle, the third winding forming a full circle of 360 degrees and having sharp edges pointing downwards for actually cutting and removing part of the vessel wall, without occlusion of the receptor vessel.

8. Method according to claim 6, wherein the vessels are blood vessels.

9. Method according to claim 6, wherein the vessels are ureters.

10. Method according to claim 6, wherein the vessels are tracheae.

* * * * *